*(12)* United States Patent
Lohri

(10) Patent No.: US 7,485,731 B2
(45) Date of Patent: Feb. 3, 2009

(54) METHOD FOR PREPARING ENANTIOMERICALLY PURE 4-PYRROLIDINOPHENYLBENZYL ETHER DERIVATIVES

(75) Inventor: Bruno Lohri, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 435 days.

(21) Appl. No.: 11/370,450

(22) Filed: Mar. 8, 2006

(65) Prior Publication Data

US 2006/0211869 A1    Sep. 21, 2006

(51) Int. Cl.
*C07D 207/04* (2006.01)
*C07D 207/12* (2006.01)

(52) U.S. Cl. .................. 548/550; 548/541; 548/543

(58) Field of Classification Search .................. 548/541, 548/543, 550
See application file for complete search history.

(56) References Cited

U.S. PATENT DOCUMENTS 7,037,935 B2 *   5/2006   Iding et al.   ................. 514/423
7,122,562 B2 *  10/2006   Iding et al.   ................. 514/343

FOREIGN PATENT DOCUMENTS

WO   WO 97/33572    9/1997
WO   WO 01/34172    5/2001
WO   WO 2004/026825  4/2004

OTHER PUBLICATIONS

Bach, et al. Proc. Natl. Acad. Sci. USA 85:4934-4938 (1988).
Cesura, et al., A., Prog. Drug Research 38:171-297 (1992).
Fowler, et al. J. Neural. Transm. 49:1-20 (1980).
Benedetti, et al. Biochem. Pharmacol. 38:555-561 (1989).
Saura, et al. Neuroscience 70:755-774 (1996).
Bentue-Ferrer, et al. CNS Drugs 6(3): 217-236 (1996).
Gardner, et al. J. Clin. Psychiatry 57(3):99-104 (1996).
Schlaeger, E. J., & Christensen, K., Cytotechnology 30:71-83 (1999).
Zhou, et al., Analytical Biochemistry 253:169-174 (1997).
Wang, et al., Synlett, vol. 9, pp. 1485-1487, 2001.
Bell, et al., Tetrahedron Letters, vol. 41, pp. 1141-1145 (2000).
Heitz, et al., J. Org. Chem. vol. 54, pp. 2591-2596 (1989).
Liu, et al., Chinese Journal of Organic Chemistry, vol. 24, No. 6, pp. 637-640 (2003).
Calvisi, et al., Synlett, pp. 71-74 (1997).

* cited by examiner

*Primary Examiner*—Golam M Shameem
(74) *Attorney, Agent, or Firm*—George W. Johnston; Patricia S. Rocha-Tramaloni; Kimberly J. Prior

(57) ABSTRACT

The invention relates to a method for preparing enantiomerically pure 4-pyrrolidinophenylbenzyl ether derivatives of formula I:

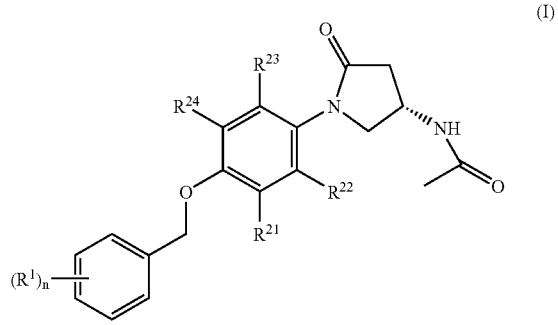

wherein $R^1$, $R^{21}$, $R^{22}$, $R^{23}$, $R^{24}$ and n are as defined the description and claims and to intermediates and salts thereof useful in the method of the invention.

10 Claims, No Drawings

METHOD FOR PREPARING ENANTIOMERICALLY PURE 4-PYRROLIDINOPHENYLBENZYL ETHER DERIVATIVES

PRIORITY TO RELATED APPLICATIONS

This application claims the benefit of European Application No. 05102028.7, filed Mar. 15, 2005, which is hereby incorporated by reference in its entirety.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes [Bach et al., Proc. Natl. Acad. Sci. USA 85:4934-4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171-297 (1992)]. Brain MAO-B activity appears to increase with age. This increase has been attributed to the gliosis associated with aging [Fowler et al., J. Neural. Transm. 49:1-20 (1980) ]. Additionally, MAO-B activity is significantly higher in the brains of patients with Alzheimer's disease [Dostert et al., Biochem. Pharmacol. 38:555-561 (1989)] and it has been found to be highly expressed in astrocytes around senile plaques [Saura et al., Neuroscience 70:755-774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentué-Ferrer et al. [CNS Drugs 6:217-236 (1996)]. Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99-104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

Compounds of formula (I)

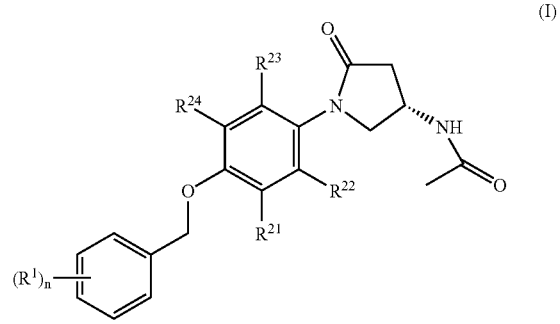

wherein $R^1$ is halogen, halogen-$(C_1$-$C_6)$-alkyl, cyano, $(C_1$-$C_6)$-alkoxy or halogen-$(C_1$-$C_6)$-alkoxy;

$R^{21}$, $R^{22}$, $R^{23}$ and $R^{24}$ are each independently selected from the group consisting of hydrogen and halogen; and n is 0, 1, 2 or 3 are selective monoamine oxidase B inhibitors.

The preparation of MAO-B inhibitors of formula (I) has been disclosed in commonly owned patent application WO 2004/026825. However, that patent application does not disclose the process of the instant invention.

SUMMARY OF THE INVENTION

The invention provides a method for preparing enantiomerically pure 4-pyrrolidinophenylbenzyl ether derivatives. The method produces compounds of formula (I) with high yields and purity. The invention also provides intermediates that are useful in the method of the invention and salts thereof.

More particularly, the present invention provides a method for preparing enantiomerically pure 4-pyrrolidino derivatives of the formula (I):

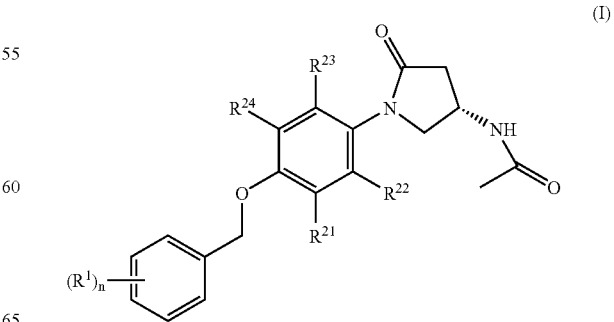

said method comprising reacting a compound of formula (II):

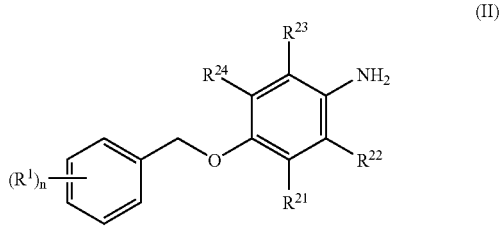

with (S)-N-(5-oxo-tetrahydro-furan-3-yl)-acetamide to obtain a compound of formula (III):

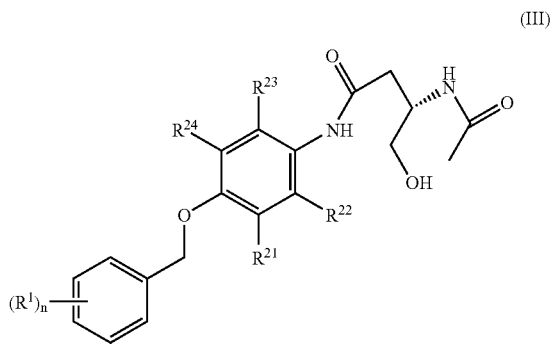

and then cyclizing the compound of formula (III) to obtain the compound of formula (I);

wherein
R$^1$ is halogen, halogen-(C$_1$-C$_6$)-alkyl, cyano, (C$_1$-C$_6$)-alkoxy or halogen-(C$_1$-C$_6$)-alkoxy;
R$^{21}$, R$^{22}$, R$^{23}$ and R$^{24}$ are each independently selected from the group consisting of hydrogen and halogen; and
n is 0, 1, 2 or 3.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

In the structural formulae presented herein a wedged bond ( ` ) denotes that the substituent is above the plane of the paper.

In the structural formulae presented herein a dotted bond ( ······· ) denotes that the substituent is below the plane of the paper.

The term "(C$_1$-C$_6$)-alkyl" used in the present application denotes straight-chain or branched saturated hydrocarbon residues with 1 to 6 carbon atoms, such as methyl, ethyl, n-propyl, i-propyl, n-butyl, sec-butyl, t-butyl, and the like, preferably with 1 to 3 carbon atoms. Accordingly, the term "(C$_1$-C$_3$)-alkyl" means a straight-chain or branched saturated hydrocarbon residue with 1 to 3 carbon atoms.

"(C$_1$-C$_6$)-Alkoxy" means the residue —O—R, wherein R is a lower alkyl residue as defined herein.

Examples of alkoxy radicals include, but are not limited to, methoxy, ethoxy, isopropoxy, and the like.

The term "halogen" denotes fluorine, chlorine, bromine and iodine.

"Halogen-(C$_1$-C$_6$)-alkyl" or "halogen-(C$_1$-C$_6$)-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. "Halogenalkoxy" includes trifluoromethyloxy.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, compounds of formula I can be converted into pharmaceutically acceptable salts. It should be understood that pharmaceutically acceptable salts are included in the present invention.

The expression "enantiomerically pure" denotes an enantiomeric ratio of the desired enantiomer:undesired enantiomer of at least 95:5, preferably at least 98:2 and still more preferably at least 99.9:0.1. The enantiomeric ratio can be determined by HPLC on a chiral column.

The present invention provides a method for preparing enantiomerically pure 4-pyrrolidino derivatives of the formula (I):

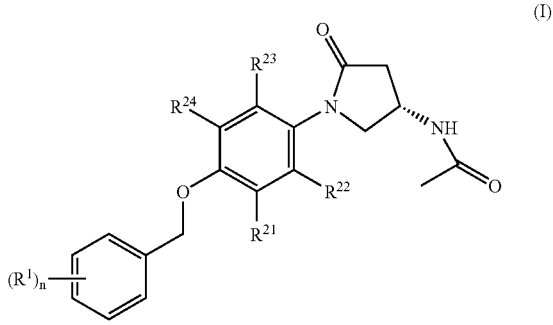

said method comprising reacting a compound of formula (II):

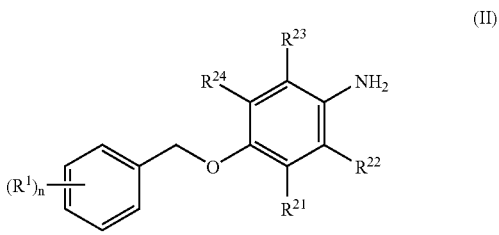

with (S)-N-(5-oxo-tetrahydro-furan-3-yl)-acetamide to obtain a compound of formula (III):

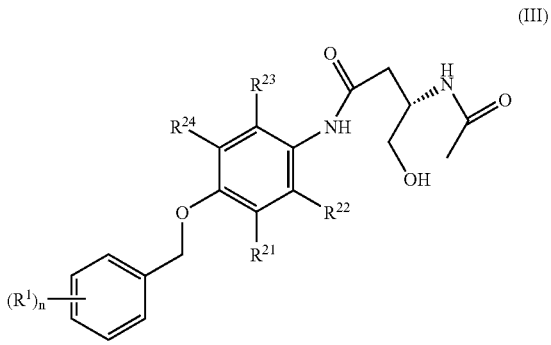

and then cyclizing the compound of formula (III) to obtain the compound of formula (I);

wherein
R$^1$ is halogen, halogen-(C$_1$-C$_6$)-alkyl, cyano, (C$_1$-C$_6$)-alkoxy or halogen-(C$_1$-C$_6$)-alkoxy;
R$^{21}$, R$^{22}$, R$^{23}$ and R$^{24}$ are each independently selected from the group consisting of hydrogen and halogen; and
n is 0, 1, 2 or 3.

The reaction between the compound of formula (II) and (S)-N-(5-oxo-tetrahydro-furan-3-yl)-acetamide to obtain the compound of formula (III) can be performed in a solvent, e.g. tetrahydrofuran, in particular dry tetrahydrofuran. The reaction also can be performed in the absence of a solvent.

Further a base can be used, including lithium bis(trimethylsilyl)amide or sodium bis(trimethylsilyl)amide, e.g. in the form of an about 1 M solution, preferably in a solvent such as tetrahydrofuran. It is to be understood that while a base can be used, the reaction also can be conducted in the absence of a base.

The resulting compound of formula (III) can be isolated and purified using conventional methods and equipments (e.g. extraction, precipitation, etc.).

The cyclization of the compound of formula (III) into the compound of formula (I) according to the invention can be performed using a conventional Mitsunobu reagent, such as azodicarboxylates which can be selected from the group consisting of di-tert-butyl azodicarboxylate (DBAD), diethyl azodicarboxylate (DEAD), diisopropyl azodicarboxylate (DIAD) or 1,1'-(azodicarbonyl)dipiperidine in combination with tri-n-butylphosphine. A solvent can suitably used in the cyclization, including tetrahydrofuran, but is not required.

The description of a suitable cyclization according to the Mitsunobu method is given, for example, in I. M. Bell et al., Tetrahedron. Lett. 2000, 41, 1141-1145.

The cyclization of the compound of formula (III) into the compound of formula (I) according to the invention can alternatively be performed via conversion of compound of formula (III) into a sulfonate, e.g. using mesylchloride (MsCl) in triethylamine (Et$_3$N), according to the method in M. P. Heitz, et al., J. Org. Chem. 1989, 54, 2591-2596.

The compound of formula (II) can be prepared as described in commonly owned patent application WO 2004/026825, the disclosure of which is incorporated by reference herein.

(S)-N-(5-oxo-tetrahydro-furan-3-yl)-acetamide can be prepared starting from commercially available material as described by Q.-Z. Liu et al. Youji Huaxue, 2004, 24, 637, and G. Calvisi et al., Synlett 1997, 71. A possible route for the preparation of (S)-N-(5-oxo-tetrahydro-furan-3-yl)-acetamide is described in example B, starting from N-acetyl-L-aspartic anhydride, the preparation of which is described in example A.

In certain embodiments of the method according to the invention, the compound of formula (II) is 4-(3-fluoro-benzyloxy)-phenylamine, the compound of formula (III) is (S)-3-acetylamino-N-[4-(3-fluoro-benzyloxy)-phenyl]-4-hydroxy-butyramide, and the compound of formula (I) is (S)-N-{1-[4-(3-fluoro-benzyloxy)-phenyl]-5-oxo-pyrrolidin-3-yl}-acetamide.

The invention also encompasses the intermediate compounds of formula (III):

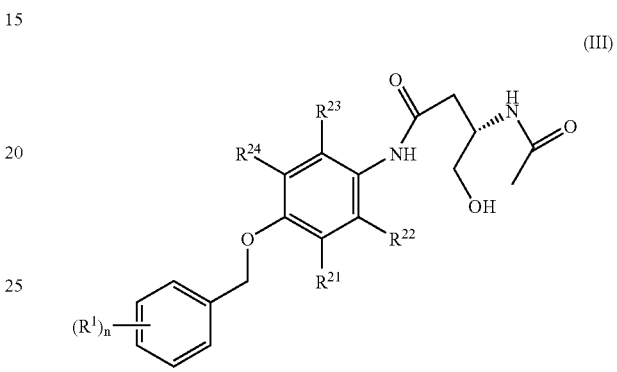

wherein
R$^1$ is halogen, halogen-(C$_1$-C$_6$)-alkyl, cyano, (C$_1$-C$_6$)-alkoxy or halogen-(C$_1$-C$_6$)-alkoxy;
R$^{21}$, R$^{22}$, R$^{23}$ and R$^{24}$ are each independently selected from the group consisting of hydrogen and halogen; and
n is 0, 1, 2 or 3.

As mentioned hereinabove, in certain embodiments of the invention, the compound of formula (III) is (S)-3-acetylamino-N-[4-(3-fluoro-benzyloxy)-phenyl]-4-hydroxy-butyramide.

The compounds of formula (I) are, as already mentioned above, monoamine oxidase B inhibitors and can be used for the treatment of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity, as well as the prevention and treatment of withdrawal syndromes induced by abuse of alcohol, nicotine and other addictive drugs. Other treatable indications may be peripheral neuropathy caused by cancer chemotherapy (WO 97/33,572), reward deficiency syndrome (WO 01/34,172), or the treatment of multiple sclerosis (WO 96/40,095), and other neuroinflammatory diseases.

The compounds of formula (I) are especially useful for the treatment of Alzheimer's disease and senile dementia.

The pharmacological activity of the compounds was tested using the following method: The cDNAs encoding human MAO-A and MAO-B were transiently transfected into EBNA cells using the procedure described by Schlaeger and Christensen [Cytotechnology 15:1-13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169-174 (1997)]. Briefly, membrane aliquots were incubated in 0.1 M potassium phosphate buffer, pH 7.4, for 30 min at 37° C. containing different concentrations of the compounds. After this period, the enzymatic reaction was started by the addition of the MAO substrate tyramine together with 1 U/ml horse-radish peroxidase (Roche Biochemicals) and 80 µM N-acetyl-3,7-dihydroxyphenoxazine (Amplex Red, Molecular Probes). The samples were further incubated for 30 min at 37° C. in a final volume of 200 µl and absorbance was then determined at a wavelength of 570 nm using a SpectraMax plate reader (Molecular Devices). Background (non-specific) absorbance was determined in the presence of 10 µM clorgyline for MAO-A or 10 µM L-deprenyl for MAO-B. $IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of preferred compounds of formula (I) as measured in the assay described above are in the range of 1 µM or less, typically 0.1 µM or less, and ideally 0.02 µM or less.

The present invention also provides pharmaceutical compositions containing compounds of formula (I) and a pharmaceutically acceptable carrier. Such pharmaceutical compositions can be in the form of tablets, coated tablets, dragées, hard and soft gelatin capsules, solutions, emulsions, suspensions, suppositories or injectable solutions.

The pharmaceutical compositions of the invention, in addition to one or more compound of formula (I), contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of formula (I) can be formulated into pharmaceutical compositions by bringing one or more compounds of formula (I) and, if desired, one or more other therapeutically valuable substance into a galenical dosage form together with one or more therapeutically inert carrier.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided for illustration of the invention. They should not be considered as limiting the scope of the invention, but merely as being representative thereof. The abbreviation "RT" means "room temperature".

Synthesis of Starting Products

EXAMPLE A

Preparation of N-acetyl-L-aspartic anhydride

A stirred suspension of N-Acetyl-L-aspartic acid (35.0 g, 199.9 mmol) in acetic anhydride (100 mL, 1.06 mol) was heated to 80° C. for ~1 h until all the solid material had dissolved. The heating bath was removed, and the reaction mixture was stirred 4 h at ambient temperature. The product was collected by filtration and washed with tert-butyl methyl ether to afford N-acetyl-L-aspartic anhydride (27.8 g, 88%) as white crystals, $[\alpha]_D$ −49.0° (c=2.5, $Ac_2O$).

EXAMPLE B

Preparation of (S)-N-(5-oxo-tetrahydro-furan-3-yl)-acetamide

To a stirred suspension of sodium borohydride (1.264 g, 33.41 mmol) in tetrahydrofuran (100 mL), N-acetyl-L-aspartic anhydride (5.0 g, 31.82 mmol, prepared as described in example A) was added in five portions at 0° C. over 1 h. The white suspension was warmed to room temperature, stirred for 3 h and cooled again to 0° C. Cold water (~50 mL) was slowly added to the stirred mixture while the temperature was allowed to reach 15° C. After stirring overnight at room temperature, tetrahydrofuran was evaporated in vacuo. The residual aqueous solution was diluted with water to a volume of 100 mL and passed through a Dowex 50X8 ion exchange column (100 g). The ion exchange column was rinsed with water (3×100 mL). The resulting aqueous solution was concentrated in vacuo and the residue was taken up in a mixture of toluene (30 mL) and methanol (70 mL). The solvent was evaporated in vacuo. This procedure was repeated, i.e. the residue was taken up in toluene-methanol and concentrated again another three times. The remaining colorless oil (5.4 g) which consisted of a mixture of hydroxy-acid and lactone was dissolved in acetic acid (54 mL). Toluene (54 mL) was added and the solution was stirred at 110° C. for 2.5 h. After this time, all hydroxy-acid was cyclized to the desired lactone according to GC analysis of a reaction sample which had been concentrated and silylated. The reaction mixture was concentrated in vacuo. Three times the residue was taken up in toluene and concentrated again to give the crude product (4.2 g) as a white solid. For purification, the crude product was dissolved in acetonitrile (30 mL). Toluene (60 mL) was added to the solution and acetonitrile was partly removed from the mixture in vacuo, until the product started to crystallize. The product was collected by filtration, washed with toluene and tert-butyl methyl ether and dried in vacuo to afford (S)-N-(5-oxo-tetrahydro-furan-3-yl)-acetamide (3.8 g, 83% based on N-acetyl-L-aspartic anhydride) as white crystals. The structure of the compound was confirmed by 1H-NMR, MS, IR. and elemental analysis.

Preparation of Intermediates of Formula (III)

EXAMPLE C

Preparation of (S)-3-acetylamino-N-[4-(3-fluoro-benzyloxy)-phenyl]-4-hydroxy-butyramide Using LiHMDS as the Base To a stirred solution of (S)-N-(5-oxo-tetrahydro-furan-3-yl)-acetamide (1.0 g, 6.99 mmol, prepared as described in example B) and 4-(3-fluoro-benzyloxy)-phenylamine (1.366 g, 6.29 mmol) in dry tetrahydrofuran, a 1 M solution (17.47 mL, 17.47 mmol) of lithium bis(trimethylsilyl)amide in tetrahydrofuran was added dropwise at 0° C. over 15 min. The cooling bath was removed and stirring was continued at ambient temperature. After 3.5 h total reaction time, a 10% aqueous ammonium chloride solution (10 mL) was added dropwise, followed by addition of dichloromethane (20 mL). The precipitated product was collected by filtration to afford, after drying in vacuo, (S)-3-acetylamino-N-[4-(3-fluoro-benzyloxy)-phenyl]-4-hydroxy-butyramide (2.0 g, 79%) as white crystals in a purity of 96.9% (HPLC area). The structure of the compound was confirmed by 1H-NMR, MS and IR.

EXAMPLE D

Preparation of (S)-3-acetylamino-N-[4-(3-fluoro-benzyloxy)-phenyl]-4-hydroxy-butyramide Using NaHMDS as the Base The reaction was carried out as described in example C. However, the 1 M solution of lithium bis(trimethylsilyl)amide in tetrahydrofuran was replaced by a 2 M solution (8.73 mL, 17.47 mmol) of sodium bis(trimethylsilyl)amide in tetrahydrofuran. The reaction time was 4.5 h to afford, after isolation of the product, (S)-3-acetylamino-N-[4-(3-fluoro-benzyloxy)-phenyl]-4-hydroxy-butyramide (1.45 g, 58%) as white crystals in a purity of 95.4% (HPLC area).

Preparation of Compounds of Formula (I)

Preparation of (S)-N-{1-[4-(3-fluoro-benzyloxy)-phenyl]-5-oxo-pyrrolidin-3-yl}-acetamide To a stirred solution of di-tert-butyl azodicarboxylate (958 mg, 4.16 mmol) in tetrahydrofuran (8 mL) tri-n-butylphosphine (886 mg, 4.16 mmol) was added. The resulting solution was stirred at room temperature for 5 min and cooled to 0° C. At this temperature, (S)-3-acetylamino-N-[4-(3-fluoro-benzyloxy)-phenyl]-4-hydroxy-butyramide (1.0 g, 2.77 mmol, prepared as described in example C) was added as a solid in several portions over 5 min. Tetrahydrofuran (4 mL) was used for rinsing. The cooling bath was removed, and stirring was continued at room temperature. After 3 h total reaction time, the reaction mixture was extracted using saturated aqueous sodium bicarbonate (30 mL) and dichloromethane (40 mL). The organic phase was separated and washed with water. The aqueous phases were extracted once with fresh dichloromethane. The dichloromethane phases were combined, dried over sodium sulfate and concentrated in vacuo to give the crude product. Flash chromatography on silica gel (90 g) using dichloromethane containing 4% methanol gave a white solid (620 mg), which was dissolved in warm acetone (25 mL). The solution was concentrated in vacuo to a volume of ~3 mL. The product started to crystallize, and tert-butyl methyl ether (10 mL) was added. The suspension was kept at room temperature overnight, and the crystals were collected by filtration and dried in vacuo to afford (S)-N-{1-[4-(3-fluoro-benzyloxy)-phenyl]-5-oxo-pyrrolidin-3-yl}-acetamide (570 mg, 60%) in a purity of 98.4% (HPLC area). The enantiopurity of the product was (S)/(R)>99.9:0.1.

The invention claimed is:

1. A method for preparing enantiomerically pure 4-pyrrolidino derivatives of the formula I:

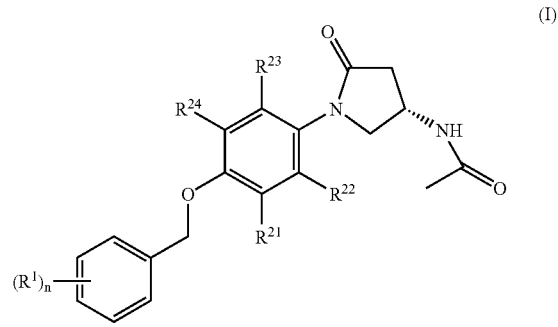

(I)

said method comprising reacting a compound of formula (II):

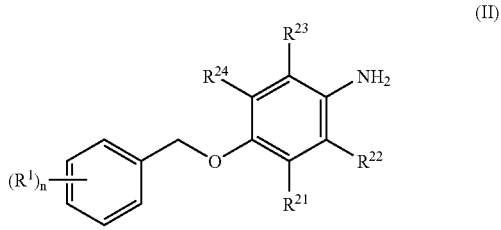

(II)

with (S)-N-(5-oxo-tetrahydro-furan-3-yl)-acetamide to obtain a compound of formula (III):

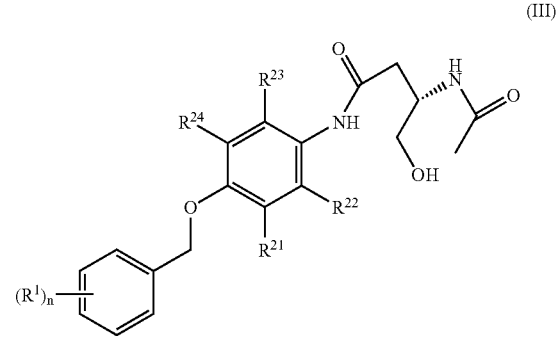

(III)

and then cyclizing the compound of formula (III) to obtain the compound of formula (I);
wherein
$R^1$ is halogen, halogen-$(C_1$-$C_6)$-alkyl, cyano, $(C_1$-$C_6)$-alkoxy or halogen-$(C_1$-$C_6)$-alkoxy;
$R^{21}$, $R^{22}$, $R^{23}$ and $R^{24}$ are each independently selected from the group consisting of hydrogen and halogen; and
n is 0, 1, 2 or 3.

2. The method of claim 1, wherein the reaction between the compound of formula (II) and (S)-N-(5-oxo-tetrahydro-furan-3-yl)-acetamide is performed in the presence of a base selected from lithium bis(trimethylsilyl)amide and sodium bis(trimethylsilyl)amide.

3. The method of claim 2, wherein the reaction between the compound of formula (II) and (S)-N-(5-oxo-tetrahydro-furan-3-yl)-acetamide is performed in the presence of tetrahydrofuran.

4. The method of claim 1, wherein the cyclization of the compound of formula (III) is performed in the presence of an azodicarboxylate in combination with tri-n-butylphosphine.

5. The method of claim 4, wherein the azodicarboxylate is selected from the group consisting of di-tert-butyl azodicarboxylate (DBAD), diethyl azodicarboxylate (DEAD), diisopropyl azodicarboxylate (DIAD) and 1,1'-(azodicarbonyl)dipiperidine.

6. The method of claim 1, wherein the cyclization of the compound of formula (III) is performed via conversion of the compound of formula (III) into a sulfonate.

7. The method of claim 6, wherein the cyclization of the compound of formula (III) is performed using mesylchloride (MsCl) in triethylamine ($Et_3N$).

8. The method of claim 1, wherein the compound of formula (II) is 4-(3-fluoro-benzyloxy)-phenylamine, the compound of formula (III) is (S)-3-acetylamino-N-[4-(3-fluoro-benzyloxy)-phenyl]-4-hydroxy-butyramide, and the compound of formula (I) is (S)-N-{1-[4-(3-fluoro-benzyloxy)-phenyl]-5-oxo-pyrrolidin-3-yl}-acetamide.

9. A compound of formula (III):

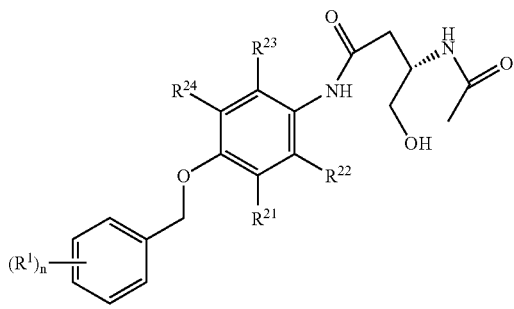

wherein
$R^1$ is halogen, halogen-$(C_1$-$C_6)$-alkyl, cyano, $(C_1$-$C_6)$-alkoxy or halogen-$(C_1$-$C_6)$-alkoxy;
$R^{21}$, $R^{22}$, $R^{23}$ and $R^{24}$ are each independently selected from the group consisting of hydrogen and halogen; and
n is 0, 1, 2 or 3.

10. A compound of claim 9, which is (S)-3-acetylamino-N-[4-(3-fluoro-benzyloxy)-phenyl]-4-hydroxy-butyramide.

* * * * *

UNITED STATES PATENT AND TRADEMARK OFFICE
CERTIFICATE OF CORRECTION

PATENT NO. : 7,485,731 B2  Page 1 of 1
APPLICATION NO. : 11/370450
DATED : February 3, 2009
INVENTOR(S) : Bruno Lohri It is certified that error appears in the above-identified patent and that said Letters Patent is hereby corrected as shown below:

Title Page, item [30]

The Foreign Application Priority Data is missing. The Foreign Application Priority Data should read -- 03/15/2005 (EP)....................05102028.7 --.

Signed and Sealed this

Thirty-first Day of March, 2009

JOHN DOLL
*Acting Director of the United States Patent and Trademark Office*